(12) United States Patent
Mishima et al.

(10) Patent No.: US 7,211,071 B2
(45) Date of Patent: May 1, 2007

(54) DIAPER PACKAGE

(75) Inventors: Yoshitaka Mishima, Kagawa-ken (JP); Tomoharu Hino, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 104 days.

(21) Appl. No.: 11/013,408

(22) Filed: Dec. 17, 2004

(65) Prior Publication Data
US 2005/0133395 A1 Jun. 23, 2005

(30) Foreign Application Priority Data
Dec. 18, 2003 (JP) ............................. 2003-421376

(51) Int. Cl.
*A61F 13/15* (2006.01)
*B65D 73/00* (2006.01)
*B65D 85/62* (2006.01)

(52) U.S. Cl. .................. 604/385.201; 604/385.01; 206/494; 206/499

(58) Field of Classification Search ........... 604/385.01, 604/385.02, 385.201; 206/494, 499, 440, 206/570, 362.4, 363, 812, 823
See application file for complete search history.

(56) References Cited

U.S. PATENT DOCUMENTS

| 4,966,286 | A | * | 10/1990 | Muckenfuhs | ............... | 206/494 |
|---|---|---|---|---|---|---|
| 5,150,561 | A | | 9/1992 | Muckenfuhs | | |
| 5,361,905 | A | * | 11/1994 | McQueeny et al. | ......... | 206/494 |
| 5,829,230 | A | | 11/1998 | Hartz | | |
| 7,000,764 | B2 | * | 2/2006 | Otsubo | ........................ | 206/494 |
| 2003/0106825 | A1 | * | 6/2003 | Molina et al. | ............... | 206/494 |
| 2003/0155265 | A1 | | 8/2003 | Tippey | | |

FOREIGN PATENT DOCUMENTS

| EP | 0-406-928 A1 | 1/1991 |
|---|---|---|
| EP | 0-618148 A1 | 10/1994 |
| JP | 11-501275 | 2/1999 |

* cited by examiner

*Primary Examiner*—Jacqueline F. Stephens
(74) *Attorney, Agent, or Firm*—Morrison & Foerster LLP

(57) ABSTRACT

A diaper package is composed of a plurality of disposable diapers and a flexible packing bag forming top and bottom walls, and front, rear and laterally opposed walls printed with display elements. These diapers are arranged between the laterally opposed walls to form a row extending between these laterally opposed walls in such a manner that respective crotch regions of these diapers face the rear wall while respective waist-surrounding end portions of these diapers face the front wall. A radius of curvature of the corners is longer than a radius of curvature of the corners so that a range in which the package can be visually recognized from the side of the front wall is larger than a range in which the package can be visually recognized from the side of the rear wall.

6 Claims, 10 Drawing Sheets

DIAPER PACKAGE

BACKGROUND OF THE INVENTION

The present invention relates to a diaper package comprising compressed flexible disposable diapers and a flexible packing bag adapted to contain a plurality of these disposable diapers.

There has already been proposed, in a published Japanese translation of PCT international publication for patent application No. 1999-501275 (hereinafter referred to as "Citation"), a diaper package consisting of a plurality of disposable diapers each comprising a liquid-pervious topsheet, a liquid-impervious backsheet and a liquid-absorbent core interposed between these two top- and backsheets, and a flexible film adapted to pack such plurality of diapers wherein the film defines top and bottom walls spaced from each other in vertical direction, front and rear walls and two side walls extending between those top and bottom walls and wherein those diapers are compressively packed within a space surrounded by these walls (See Citation). Each of these diapers has front and rear waist regions and a crotch region along which the front and rear waist regions are contiguous to each other. The diaper further includes front and end portions lying opposed to the crotch region and defining upper end portions of the front and rear waist regions, respectively. The diaper is folded back along the crotch region so that the front and rear waist regions and consequently the front and rear end portions also are placed one upon another.

In this package of prior art, the top and bottom walls, the front and rear walls and the laterally opposed walls are substantially orthogonal one to another so as to form a hexahedron and, more specifically, this package has a three-dimensional shape of a rectangular parallelepiped which is relatively long in the vertical direction. In this diaper package, these diapers are arranged with the waist regions thereof placed against one another to form first and second rows extending the side walls. These rows are placed upon each other in the vertical direction. In the first row, the respective crotch regions' bottoms aligned one with another between the side walls face the top wall. In the second row, the respective crotch regions' bottoms aligned one with another between the side walls face the bottom wall. These two rows are placed upon each other in such a manner that the front and rear end portions of the respective diapers in the first row are placed against the front and rear end portions of the respective diapers in the second row. In the first and second rows, respectively, the diapers lying on both ends in the first and second rows have the waist regions as well as the front or rear end portion are placed against the side walls.

The package disclosed in Citation is three-dimensionally shaped in a rectangular parallelopipedon, so a range in which the package can be visually recognized when the front wall is seen head-on is substantially the same as a range in which the package can be visually recognized when the rear wall is seen head-on. In addition, impression left after the front wall has been seen head-on is not different from impression left after the rear wall has been seen head-on. As for the shape, this package of prior art has not a sufficiently predominant feature to attract consumer's attention and can not leave the consumer with visually impactful impression. Therefore, it is difficult for this package of prior art to improve an advertising function and a quality displaying function. Furthermore, assumed that desired display elements such as a trade name as well as a quality of the package, illustration and image are printed serially on the front wall and the side walls, these display elements will get chipped in the vicinity of corners defined by cross lines between the front walls and the side walls when the front wall is seen head-on. The range in which the display elements may be serially printed is thus limited to respective areas of the front wall and the side walls and it is impossible to print the display elements serially in a range larger than each of these walls.

SUMMARY OF THE INVENTION

In view of the problem as has been described above, it is an object of the present invention to provide a diaper package adapted to leave the consumer with a visually impactful impression and to improve an advertising function as well as a quality displaying function.

According to the present invention, there is provided a diaper package composed of a plurality of disposable diapers each comprising a liquid-pervious topsheet, a liquid-impervious backsheet and a liquid-absorbent core having stiffness higher than these sheets and interposed between these two top- and backsheets, and a flexible packing bag adapted to pack a plurality of diapers wherein each of the diapers has first and second waist regions and a crotch region along which the first and second waist regions are contiguous to each other and a waist-surrounding end portion lying opposed to the crotch region so as to define upper end portions of the first and second waist regions, respectively and wherein the film defines top and bottom walls spaced from each other in a vertical direction, first and second walls opposed to each other and extending between the top and bottom walls and two side walls extending between the top and bottom walls so that a plurality of the diapers each folded back along the crotch region are densely packed within a space surrounded by these walls.

The diaper package according to the present invention further includes a plurality of the diapers being arranged with the waist regions thereof placed against one another to be arranged between the side walls to form a row extending between the side walls so that the respective crotch regions' bottoms aligned one with another between the side walls face the second wall and the waist-surrounding end portions of the respective diapers aligned one with another between the side walls face the first wall; a radius of curvature of a corner along which the first wall and the side walls cross each other is longer than a radius of curvature of a corner along the second wall and the side walls cross each other so that a range in which the package can be visually recognized head-on from the side of the first wall is larger than a range in which the package can be visually recognized head-on from the side of the second wall.

The present invention may includes preferred embodiments as follows:

Desired display elements are printed on outer surfaces at least the first wall and the side walls.

At least two rows of diapers are stacked on each other in the vertical direction and, in each of these rows stacked on each other, the crotch regions of the respective diapers are aligned between the side walls and face the second wall and the waist-surrounding end portions of the respective diapers are aligned between the side walls and face the first wall.

The radius of curvature of the corner along which the first wall and the side walls cross each other is in a range of 25 to 500 mm and the radius of curvature of the corner along which the second wall and the side walls is in a range of 5 to 50 mm.

A total thickness dimension of the first waist region, second waist region and crotch region is larger than a thickness dimension of the waist-surrounding end portion in each of the diapers and stiffness of the first waist region, second waist region and crotch region is higher than stiffness of the waist-surrounding end portion in each of the diapers.

The packing bag has a cylindrical shape prior to packing the diapers therein and this cylindrical packing bag is deformed so as to form the first and second walls and the side walls as the diapers are packed within the space surrounded by a cylindrical wall of the packing bag.

The diaper package according to the present invention is primarily characterized in that a radius of curvature defined by corners at which the first wall crosses the side walls is longer than the radius of curvature defined by the corners at which the second wall crosses the side walls so that a range in which the package can be visually recognized head-on from the side of the first wall is larger than a range in which the package can be visually recognized head-on from the side of the second wall. Therefore, the outer surface of the package can be visually recognized head-on from the side of the first wall. In the package, the corners at which the front wall crosses the side walls is more noticeably rounded than the corners at which the rear wall crosses the side walls, so the impression given by the package as seen head-on from the side of the front wall is remarkably different from the impression given by the package as seen head-on from the side of the rear wall. Compared to the package shaped in rectangular hexahedron, the improved shape of the package according to the invention can attract the attention of the consumer and leave the consumer with vivid impression. This package not only improves its advertising function and quality displaying function but also functions to display the article manufacturer. In this way, there is no anxiety that the manufacturer of the article might be confused with the any other manufacturers.

It is assumed that the given display elements have been printed on the outer surface of at least the first wall and the side walls. The outer surface of the package can be visually recognized in a relatively large range head-on from the first wall or from the side wall so that even if the display elements are printed continuously on the first wall and the regions of the side walls put aside toward the first wall or continuously on the side walls and the region of the first wall put aside toward the side walls, it is unlikely that these display elements might get chipped at the corners when the package is seen head-on from the side of the first wall or the side walls. Thus it is possible to print the display elements each larger than each of the first wall and the side walls on these walls without getting chipped at the corners. Compared to the package of prior art, this package can leave the consumer with further vivid impression and reliably improve an advertising function as well as a quality displaying function.

In the case of the package containing the diapers at least in two rows stacked one upon another in the vertical direction, the crotch regions of the diapers forming these rows aligned one with another between the side walls face the second wall and the waist-surrounding front and rear end portions of the diapers forming these rows aligned one with another between the side walls face the first wall. Therefore there is no anxiety that the front and rear end portions might be irregularly bent and these front and rear portions might be formed with a plurality of irregular gathers as the conventional diaper package in which the front and rear end portions arranged in each pair of the adjacent rows bear against one another in the vertical direction has been the case.

In the case of the package in which a radius of curvature in a range of 25 to 500 mm is defined by the corners at which the first wall crosses the side walls and a radius of curvature in a range of 5 to 50 mm is defined by the corners at which the second wall crosses the side walls, a range in which the package can be visually recognized head-on from the side of the first wall is larger than a range in which the package can be visually recognized head-on from the side of the side walls. Consequently, the consumer can visually recognize the outer surface of the package in a wide range head-on from the first wall as well as from the side walls and the package can leave the consumer with an improved impression.

In the case of the package arranged so that the first and second waist regions and the crotch region of each diaper constituting the diaper package have a thickness dimension larger than a thickness dimension of the waist-surrounding front and rear end portions of the diaper and the first and second waist regions and the crotch region of the diaper have a stiffness higher than a stiffness of the waist-surrounding front and rear end portions of this diaper, a slight gap is left between each pair of the adjacent waist-surrounding front and rear end portions of the diapers so that the front and rear end portions of the diapers lying in the vicinity of the corners at which the first wall crosses the side walls are bent toward a transversely middle region of the first wall. The corners 19 at which the first wall crosses the side walls can be reliably curved with a radius of curvature substantially longer than a radius of curvature defined by the corners at which the second wall crosses the side walls.

In the case of the package using film as packing material which presents a cylindrical shape prior to packing of the diapers, such cylindrical shape of film is reliably deformed to define the first wall, the second wall and the side walls as a space surrounded by a cylindrical peripheral wall of the film is packed with a plurality of diapers. Upon deformation of the cylindrical peripheral wall of the film, it is ensured that the corners at which the first wall crosses the side walls define a radius of curvature substantially longer than a radius of curvature defined by the corners at which the second wall crosses the side walls. In such aspect, the package according to the present invention is advantageous in comparison to the case in which the film as the packing material presents an initial shape of hollow rectangular hexahedron.

PREFERRED EMBODIMENTS OF THE INVENTION

Details of the diaper package according to the present invention will be more fully understood from the description given hereunder with reference to the accompanying drawings.

Figure 1:
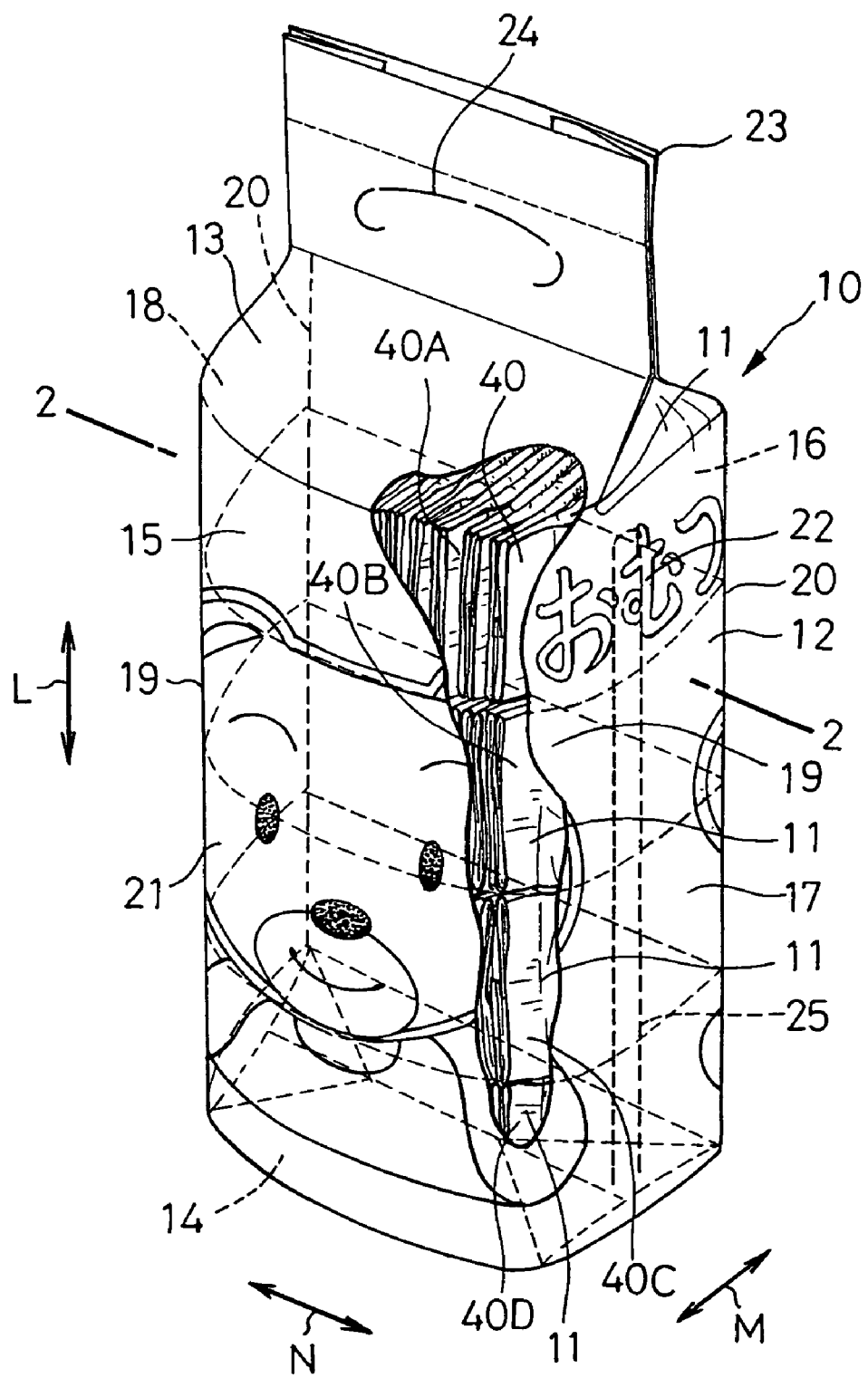
FIG. 1 is a perspective view showing a diaper package.
Figure 2:
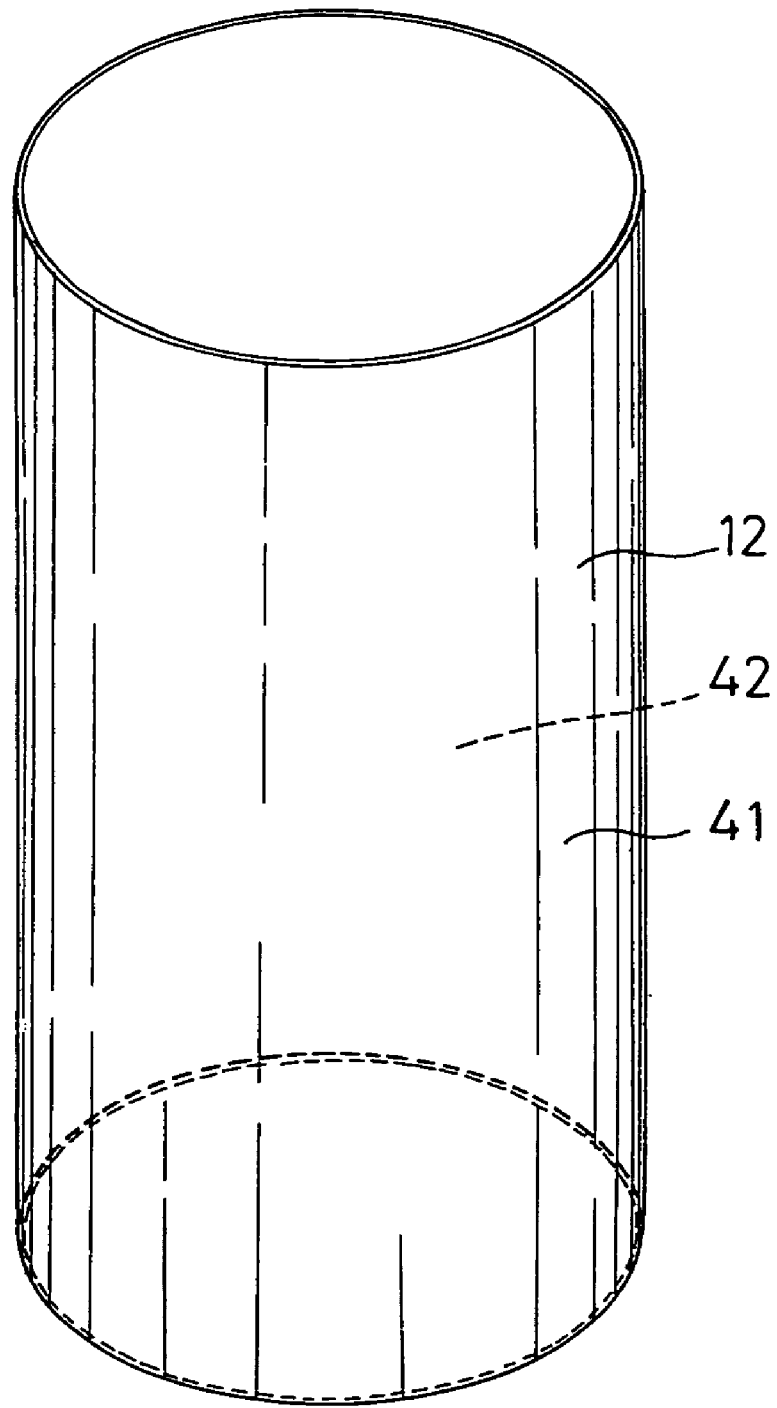
FIG. 2 is a perspective view showing a flexible packing bag in the state before packed with the diapers.
Figure 3:
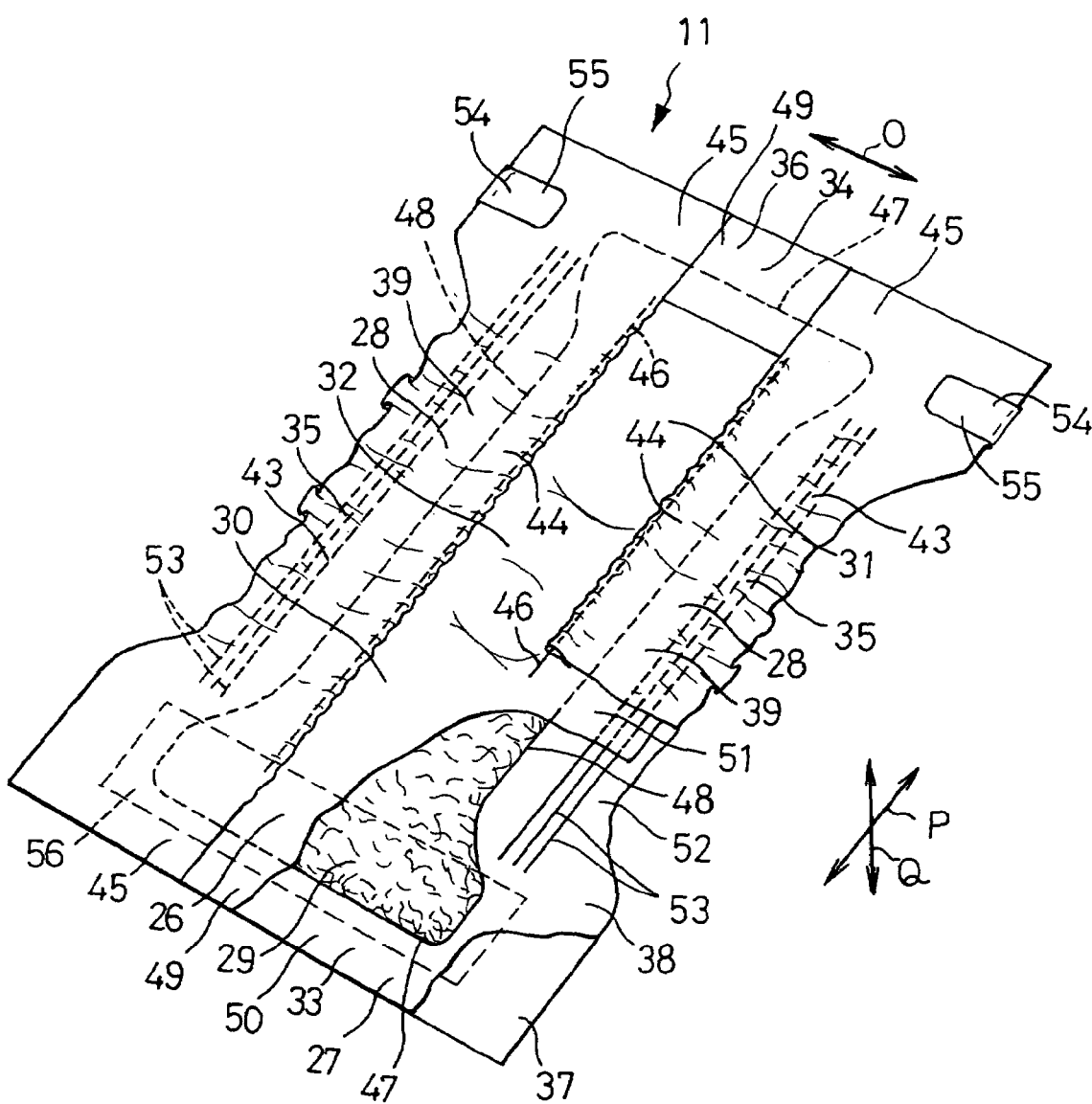
FIG. 3 is a perspective view showing a disposable diaper.
Figure 4:
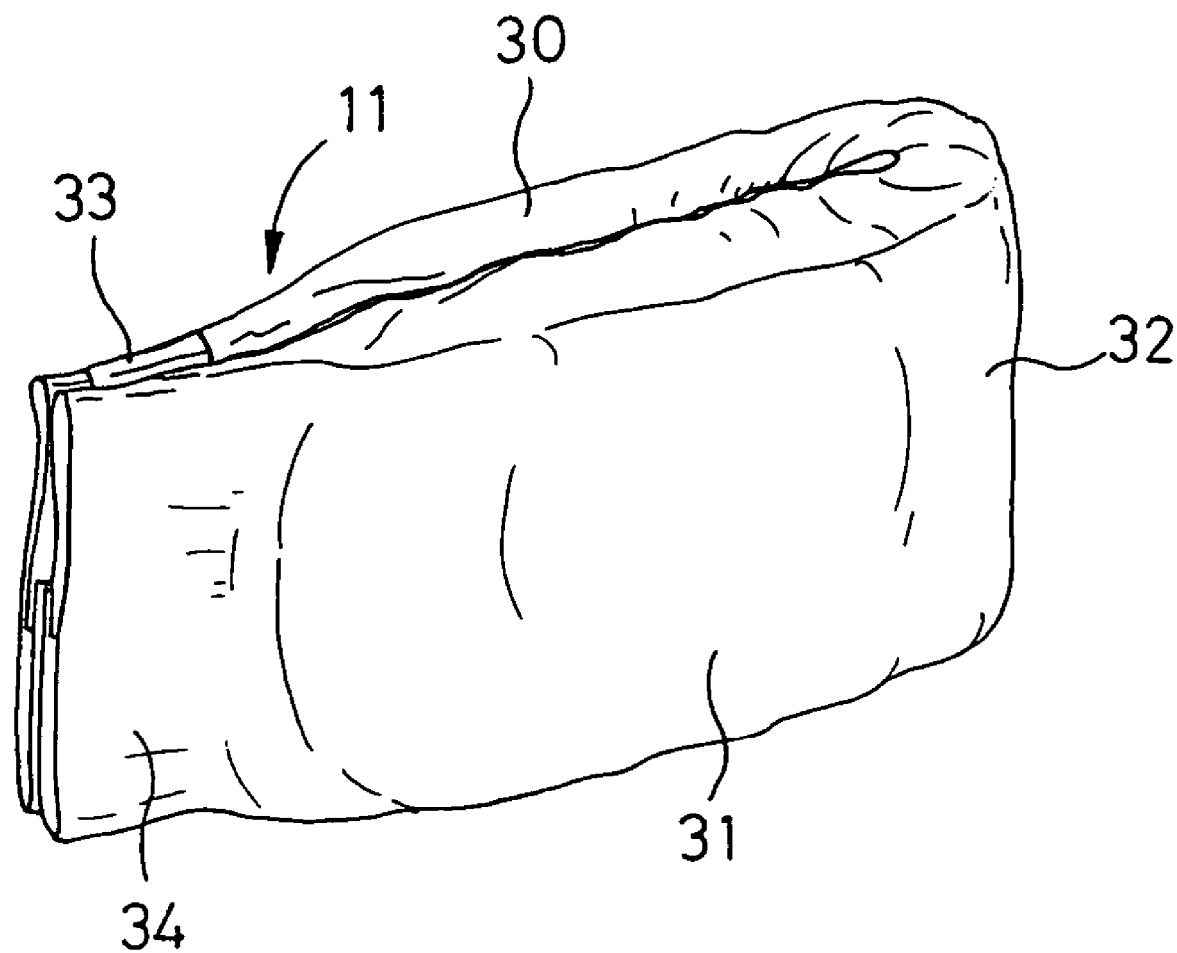
FIG. 4 is a perspective view showing the diaper immediately after taken out from the package.
Figure 5:
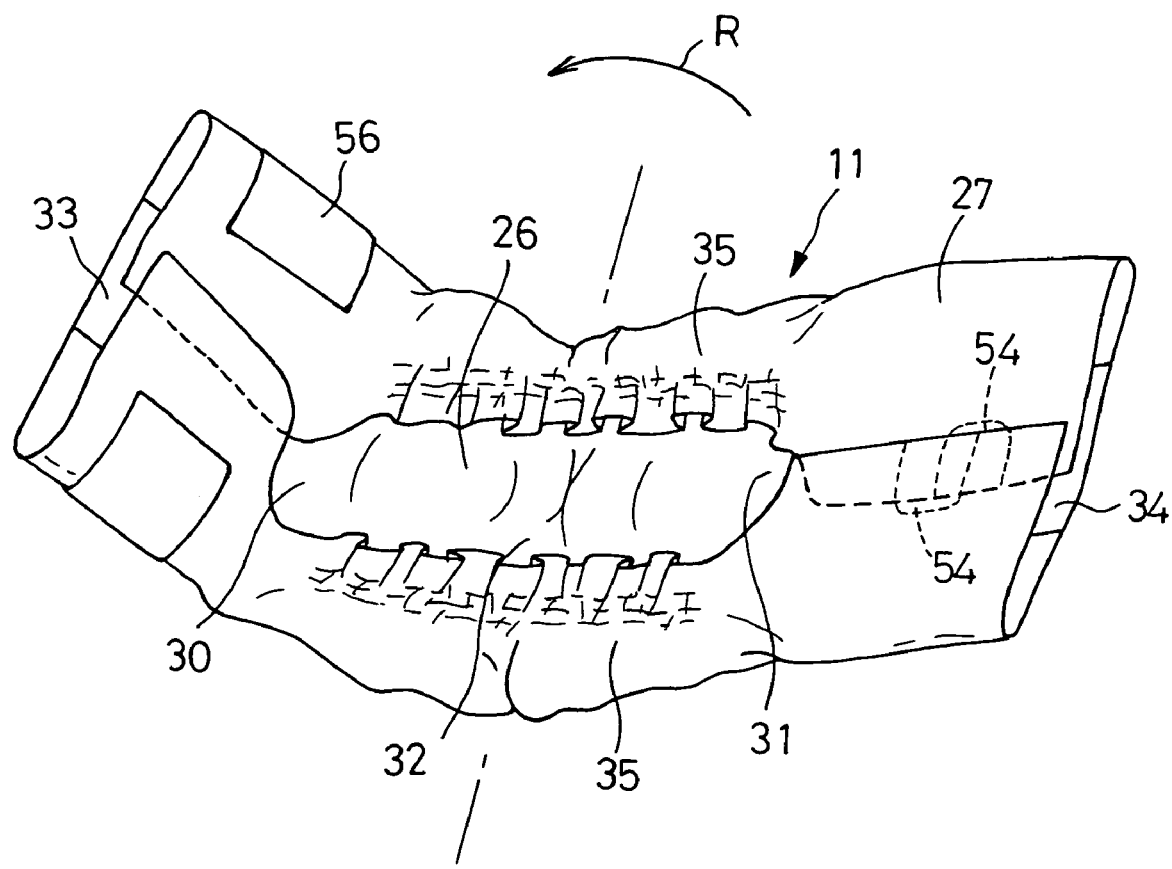
FIG. 5 is a diagram illustrating a procedure followed to fold the diaper from the state shown by FIG. 3 to the state shown by FIG. 4.

FIG. 1 is a perspective view showing a diaper package 10 with top and bottom walls 13, 15 partially cutaway, FIG. 2 is a perspective view showing a flexible packing bag 12 in the state before packed with the diapers 11, FIG. 3 is a perspective view showing a disposable diaper 11, FIG. 4 is a perspective view showing the diaper 11 after taken out from the package 10 and FIG. 5 is a diagram illustrating a procedure followed to fold the diaper 11 from the state shown in FIG. 3 to the state shown in FIG. 4. In FIG. 1, a vertical direction is indicated by an arrow L, a back-and-forth direction is indicated by an arrow M and a transverse direction is indicated by an arrow N. In FIG. 3, a transverse direction is indicated by an arrow O, a longitudinal direction is indicated by an arrow P and a thickness direction is indicated by an arrow N. As used herein "inner surfaces" of top- and backsheets 26, 27 and leak-barrier sheets 28 refer to the surfaces thereof facing a core 29 and "outer surfaces" of these sheets 26, 27, 28 refer to the surfaces thereof facing away from the core 29.

The diaper package 10 comprises a plurality of disposable diapers 11 and a flexible packing bag 12 made of a plastic film and adapted to pack these diapers 11. The packing bag 12 defines top and bottom walls 13, 14 opposed to and spaced from each other in the vertical direction, front and rear walls 15, 16 (i.e., first and second walls) extending in the vertical direction between the top and bottom walls 13, 14, side walls 17, 18 extending in the vertical direction between the top and bottom walls 13, 14, corners 19 along which the front wall 15 and the side walls 17, 18 cross one another, and corners 20 along which the rear wall 16 and the side walls 17, 18 cross one another. In the package 10, the front and rear walls 15, 16 are opposed to and spaced from each other in the back-and-forth direction and the side walls 17, 18 are opposed to and spaced from each other in the transverse direction. The interior of the package 10 surrounded by these walls 13, 14, 15, 16, 17, 18 is packed with a plurality of the diapers 11. It should be understood here that the front wall 15 corresponds to one of the first and second walls set forth in the appending Claims and the rear wall 16 corresponds to the other of the first and second walls set forth in the appending Claims.

Figure 7:
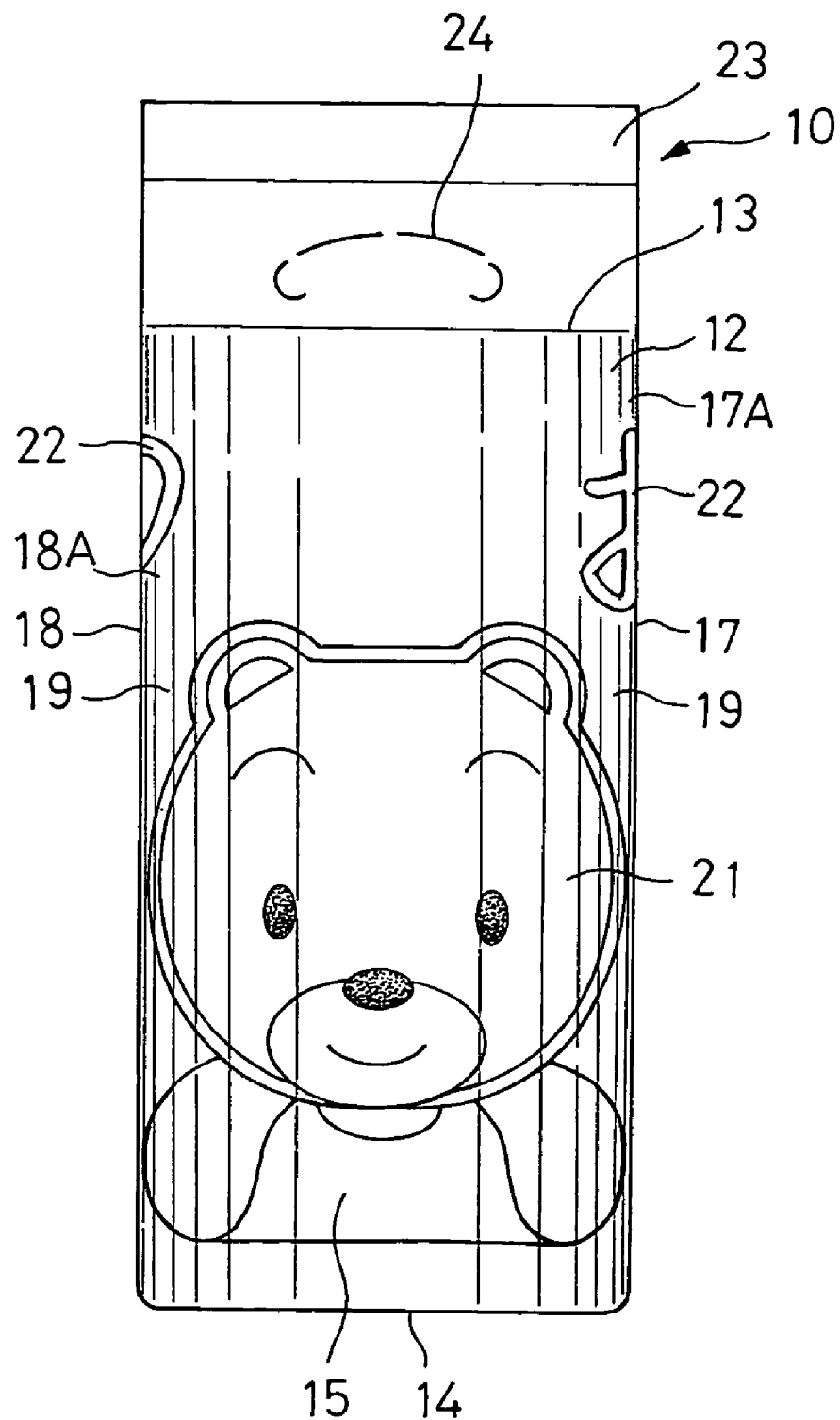
FIG. 7 is a perspective view of the package as viewed from the side of the front wall.

On the outer surfaces of the front wall 15 and respective regions 17A, 18A of the side walls 17, 18 placed aside toward the front wall 15, an image 21 (display element) of bear's head is continuously printed (See FIG. 7). Also on the outer surfaces of the rear wall 16 and respective regions 17B, 18B of the side walls 17, 18 placed aside toward the rear wall 15, an image 21 (display element) of bear's head is continuously printed (See FIGS. 9 and 10). On the outer surfaces of the side walls 17, 18 and regions of the front wall 15 placed aside toward the respective side walls 17, 18, letters 22 (display element) meaning the diaper are printed, respectively (See FIGS. 9, 10).

The top wall 13 is formed with a hand-grip 23 for the package 10. The hand-grip 23 is formed from a part of the packing bag 12 and extends upward from the top wall 13. Transversely middle zone of the hand-grip 23 is formed with a cutting-guide lines 24 extending intermittently in the transverse direction. The packing bag 12 may be broken along this cutting-guide lines 24 to form an opening into which the user may insert the fingers. One of the side walls 17 is formed with cutting-guide lines 25 intermittently extending in the vertical direction. The packing bag 12 may be broken along these cutting-guide lines 25 to form an opening through which the individual diaper 11 may be taken out from the package 10.

The diaper 11 comprises a liquid-pervious topsheet 26 facing the diaper wearer's skin, a liquid-impervious backsheet 27 facing away from the wearer's skin, a pair of liquid-impervious leak-barrier sheets 28 spaced from each other in the transverse direction and extending in the longitudinal direction, and a liquid-absorbent core 29 interposed between the top- and backsheets 26, 27 and bonded to respective inner surfaces of these sheets 26, 27. The diaper 11 has a front waist region 30, a rear waist region 31 (i.e., first and second waist regions), a crotch region 32 along which the front and rear waist regions 30, 31 are contiguous to each other, a waist-surrounding front end portion 33 (waist-surrounding end portion) lying opposite to the crotch region 32 and defining an upper end portion of the front waist region 30, a waist-surrounding rear end portion 34 (waist-surrounding end portion) lying opposite to the crotch region 32 and defining an upper end portion of the rear waist region 31, and transversely opposite lateral portions 35 extending between the front and rear end portions 33, 34. The illustrated diaper 11 is a so-called open-type diaper which has an hourglass-like planar shape in its developed state and has the front and rear waist regions 30, 31 connected to each other when the diaper 11 is put on the wearer's body. It should be understood here that the front waist region 30 corresponds to one of first and second waist regions as set forth in the appending claims and the rear waist region 31 corresponds to the other of these first and second waist regions as set forth in the appending claims.

The topsheet 26 is formed from a hydrophobic fibrous nonwoven fabric 36. The backsheet 27 is formed from a composite sheet consisting of a hydrophobic fibrous nonwoven fabric 37 and a breathable liquid-impervious plastic film 38 laminated with each other. The leak-barrier sheets 28 are formed from a repellent treated hydrophobic fibrous nonwoven fabric 39. The core 29 comprises a mixture of particulate or fibrous super-absorbent polymers and fluff pulp or a mixture of particulate or fibrous super-absorbent polymers, fluff pulp and thermoplastic synthetic resin fibers, in any case, compressed to a desired thickness. From the viewpoint of such a structure, the core 29 has stiffness higher than those of the top- and backsheets 26, 27 and the leak-barrier sheets 28. Preferably the core 29 is entirely wrapped with a tissue paper (not shown) in order to prevent the core 29 from getting out of its initial shape and to prevent the polymers from falling off.

The core 29 extends over the crotch region 32 and further into the front and rear waist regions 30, 31 and is absent in the waist-surrounding front and rear end portions 33, 34 and the transversely opposite lateral portions 35. In other words, the front and rear waist regions 30, 31 and the crotch region 32 comprise the top- and backsheets 26, 27 and the core 29 while the waist-surrounding front and rear end portions 33, 34 as well as the transversely opposite lateral portions 35 comprise the top- and backsheets 26, 27 and the leak-barrier sheets 28. In the diaper 11, therefore, the front and rear waist regions 30, 31 and the crotch region 32 in which the core 29 is present have thickness dimensions larger than those of the waist-surrounding front and rear end portions 33, 34 and the transversely opposite lateral portions. Similarly, the front and rear waist regions 30, 31 and the crotch region 32 have stiffness higher than that of the waist-surrounding front and rear end portions 33, 34 as well as the transversely opposite lateral portions 35.

As will be seen in FIG. 3, the diaper 11 immediately after taken out from the package 10 has the front and rear waist region 30, 31 placed upon each other and the waist-surrounding front and rear end portion 33, 34 also placed upon each other with the topsheet 26 lying inside. To fold the diaper 11 from the state of FIG. 3 to the state of FIG. 4, a procedure as illustrated by FIG. 5 may be followed. Specifically, the transversely opposite lateral portions 35 are folded back onto the outer surface of the topsheet 26, i.e., transversely inward and then the diaper 11 is folded in the longitudinal direction around the crotch region 32 as indicated by an arrow R so as to place the front and rear waist regions 30, 31 upon each other.

Figure 6:
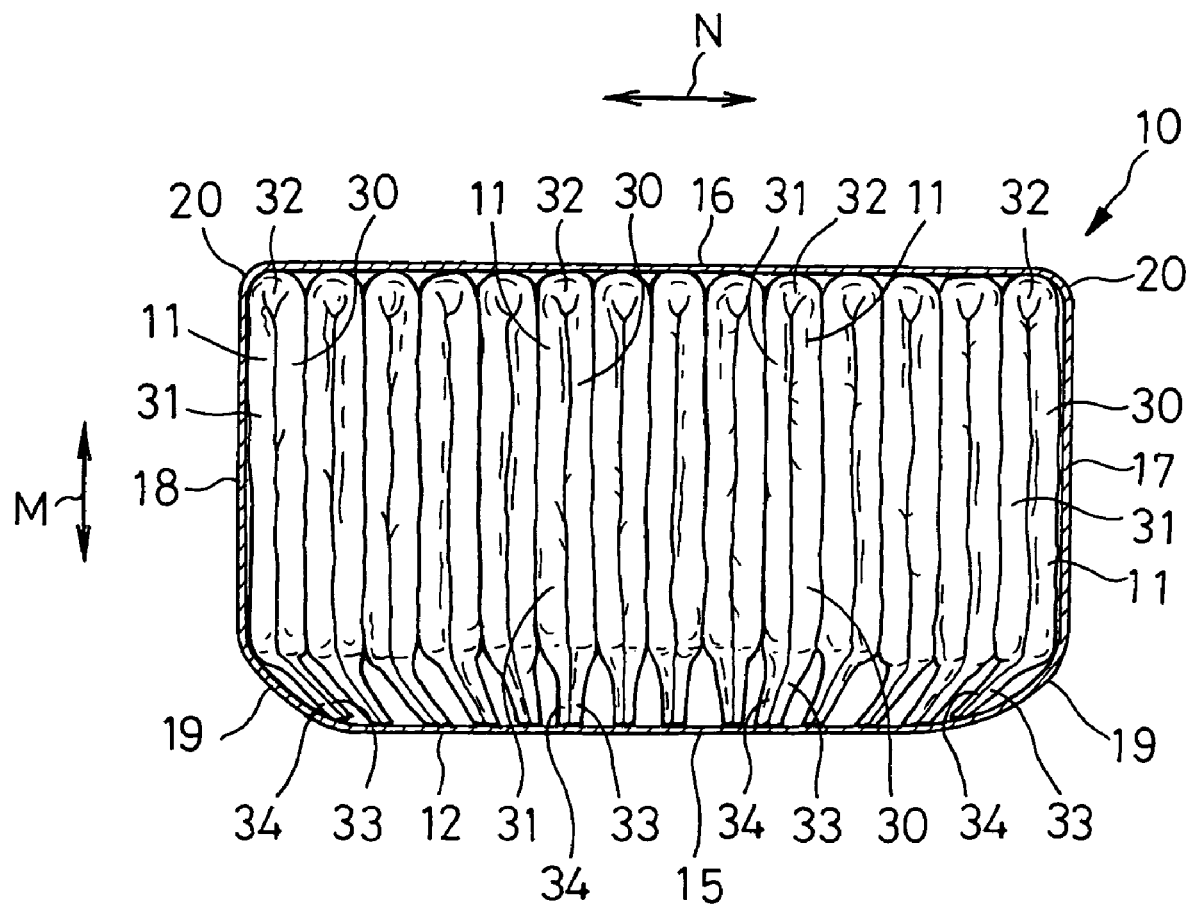
FIG. 6 is a sectional view taken along the line II—II in FIG. 1.

FIG. 6 is a sectional view taken along the line II—II in FIG. 1. In FIG. 6, a back-and-forth direction is indicated by an arrow M and a transverse direction is indicated by an arrow N. Within the package 10, a plurality of the diapers 11 are arranged between the side walls 17, 18 with the waist regions 30, 31 closely placed against one another so as to form a row 40 extending between the side walls 17, 18. Within the package 10, the respective crotch regions 32 of these diapers 11 are aligned one with another between the side walls 17, 18 and face the rear wall 16 while the respective waist-surrounding front and rear end portions 33, 34 of these diapers 11 are aligned one with another between the side walls 17, 18 and face the front wall 15. As shown in FIG. 1, first through fourth rows 40A, 40B, 40C, 40D are stacked one upon another in the vertical direction between the top and bottom walls 13, 14 of the package 10. Within the space surrounded by these walls 13, 14, 15, 16, 17, 18 of the package 10, a plurality of the diapers 11 are compactly packed in these four rows 40A, 40B, 40C, 40D compressed between the top and bottom walls 13, 14 in the vertical direction, compressed between the front and rear walls 15, 16 in the back-and-forth direction and compressed between the side walls 17, 18 in the transverse direction.

In each of the rows 4A, 4B, 4C, 4D, the respective crotch regions 32 of the diapers 11 are aligned one with another between the side walls 17, 18 and face the rear wall while the respective waist-surrounding front and rear end portions 33, 34 of the diapers 11 are aligned one with another between the side walls 17, 18 and face the front wall 15. In these rows 40A, 40B, 40C, 40D, the respective crotch regions 32 of the diapers 11 bear against the rear wall 16 and the respective waist-surrounding front and rear end portions 33, 34 of the diapers 11 bear against the front wall 15. In the first row 40A, those of the transversely opposite lateral portions 35 facing the top wall 13 bear against the top wall 13 and the waist regions 30, 31 of the diapers 11 lying on opposite ends of this row 40A bear against the respective side walls 17, 18. Those of the transversely opposite lateral portions 35 of the diapers 11 in the first row 40A facing away from the top wall 13 are placed upon those of the transversely opposite lateral portions 35 of the diapers 11 in the second row 40B facing the first row 40A. Those of the transversely opposite lateral portions 35 of the diapers 11 in the second row 40B facing away from the first row 40A are placed upon those of the transversely opposite lateral portions 35 of the diapers 11 in the third row 40C facing the second row 40B. Those of the transversely opposite lateral portions 35 of the diapers 11 in the third row 40C facing away from the second row 40B are placed upon those of the transversely opposite lateral portions 35 of the diapers 11 in the fourth row 40D facing the third row 40C. In the second and third rows 40B, 40C, the respective waist regions 30, 31 of the diapers 11 lying on opposite ends of the respective rows 40B, 40C bear against the side walls 17, 18. In the fourth row 40D, those of the transversely opposite lateral portions 35 facing the bottom wall 14 bear against this bottom wall 14 and the respective waist regions 30, 31 of the diapers 11 lying on opposite ends of the row 40D bear against the side walls 17, 18.

Within the package 10, a slight gap is left between each pair of the adjacent waist-surrounding front and rear end portions 33, 34 of the diapers 11 arranged between the side walls 17, 18 so that the front and rear end portions 33, 34 of the diapers 11 lying in the vicinity of the side walls 17, 18 are compressed by these side walls 17, 18 are bent toward a transversely middle region of the front wall 15, as will be seen in FIG. 6. On the contrary, the respective crotch regions 32 of the diapers 11 each having a thickness dimension larger than the waist-surrounding front and rear end portions and stiffness higher than the latters due to the presence of the core 29 are not bent toward the transversely middle region of the front wall 15 even if these crotch regions 32 are compressed between the side walls 17, 18. The corners 19 of the package 10 at which the front wall 15 crosses the side walls 17, 18 are curved with a relatively long radius of curvature as the front and rear end portions 33, 34 of the diapers 11 are bent in the vicinity of the corners 19. On the contrary, the corners 20 at which the rear wall 16 crosses the side walls 17, 18 are slightly curved in conformity with slightly bent the crotch regions 32 of the diapers 11 lying on respective opposite ends of the rows 40A, 40B, 40C, 40D. Thus the package 10 has a longer radius of curvature at the corners 19 than at the corners 20.

The corners 19 at which the front wall 15 crosses the side walls 17, 18 of the package 10 have a longer radius of curvature than the corners 20 at which the rear wall 16 crosses the side walls 17, 18 and a range in which the package 10 can be visually recognized head-on from the side of the front wall 15 is correspondingly larger than a range in which the package 10 can be visually recognized head-on from the side of the rear wall 16. It should be understood that the packing bag 12 has a cylindrical shape as shown in FIG. 2 before the diapers 11 are packed therein. A peripheral wall 41 of the packing bag 12 is deformed to define the front wall 15, the rear wall 16 and the side walls 17, 18 as a space 42 surrounded by the cylindrical peripheral wall 41 of the packing bag 12 is packed with a plurality of the diapers 11. After the diapers 11 have been packed in the space 42, the inner surface of an upper part of the cylindrical peripheral wall 41 may be collapsed, put flat and bonded together to form the top wall 13 and the hand-grip 23, on one hand, and a lower part of the cylindrical peripheral wall 41 may be lapped and bonded together to form the bottom wall 14, on the other hand.

Now one preferred embodiment of the diaper 11 will be described in details with reference to FIG. 3. The leak-barrier sheets 28 are laid on the outer surface of the topsheet 26 so as to occupy the transversely opposite lateral portions 35 of the diaper 11. Each of the leak-barrier sheets 28 comprises a fixed lateral portion 43 permanently bonded to the associated lateral portion 35 and extending in the longitudinal direction, a free portion 44 extending in the longitudinal direction in parallel to the fixed lateral portion 43 and normally biased to rise above the topsheet 26 and fixed longitudinally opposite end portions 45 collapsed inward as viewed in the transverse direction of the diaper 11 and permanently bonded to the waist-surrounding front and rear end portions 33, 34. The fixed lateral portion 43 and the free portion 44 extend between the waist-surrounding front and rear end portions 33, 34 of the diaper 11. A stretchable elastic member 46 extending in the longitudinal direction is contractibly attached to the free portion 44 in the vicinity of its upper edge. The elastic member 46 is stretched in the longitudinal direction at a predetermined ratio and permanently bonded in this state to the free portion 44. In the leak-barrier sheets 28, the free portions 44 contract in the longitudinal direction under a contractile force of the elastic members 46 and thereupon the free portions 44 rise above the topsheet 26 so as to form barriers against bodily discharges.

The waist-surrounding front and rear end portions 33, 34 comprise longitudinally opposite end portions 49, 50 of the top- and backsheets 26, 27 extending outward beyond longitudinally opposite ends 47 of the core 29 in the longitudinal direction and the fixed longitudinally opposite end portions 45 of the respective leak-barrier sheets 28. In the waist-surrounding front and rear end portions 33, 34, the end portions 49, 50 of the top- and backsheets 26, 27 are placed upon the end portions 45 of the leak-barrier sheets 28, respectively. The inner surface of the topsheet 26 is permanently bonded to the inner surface of the backsheets 27 while the outer surface of the topsheet 26 is permanently bonded to the inner surfaces of the leak-barrier sheets 28. The transversely opposite lateral portions 35 comprise transversely opposite lateral margins 51, 52 of the top- and backsheets 26, 27 extending outward beyond transversely opposite side edges 48 of the core 29 and the fixed lateral portions 43 of the leak-barrier sheets 28. Along the transversely opposite lateral portions 35, the lateral margins 51 of the topsheet 26 extend outward slightly beyond the side edges 48 of the core 29. Transversely opposite lateral margins 52 of the backsheet 27 and the fixed lateral portions 43 of the respective leak-barrier sheets 28 extend outward beyond the lateral margins 51 in the transverse direction. Along the transversely opposite lateral portions 35, the lateral margins 51, 52 of the top- and backsheets 26, 27 and the lateral portions 43 of the leak-barrier sheets 28 are put flat together. Inner surfaces of the top- and backsheets 26, 27 are permanently bonded together while inner and outer surfaces of the top- and backsheets 26, 27 are permanently bonded to the inner surfaces of the leak-barrier sheets 28. A plurality of leg-surrounding elastic members 53 extending in the longitudinal direction outside the transversely opposite side edges 48 of the core 29 are contractibly bonded to the transversely opposite lateral portions 35. The leg-surrounding elastic members 53 are interposed between the lateral margins 51 of the topsheet 26 and the lateral margins 52 of the backsheet 27 and stretched at a predetermined ratio in the longitudinal direction and permanently bonded in such stretched state to the respective inner surfaces of these sheets 26, 27.

The transversely opposite lateral portions 35 of the rear waist region 31 are provided with flexible tape fasteners 54 made of a plastic film. Each of the tape fasteners 54 has a fixed end portion (not shown) extending in the transverse direction and a free end portion 55. The fixed end portion is interposed between the lateral margin 52 of the backsheet 27 and the fixed lateral portion 43 of the leak-barrier sheet 28 and permanently bonded to respective inner surfaces of these sheets 27, 28. The free end portions 55 are coated on respective inner surfaces with pressure-sensitive adhesive (not shown). The free end portions 55 are folded inward as viewed in the transverse direction of the diaper 11 and temporarily fixed to the lateral portions 35 by means of pressure-sensitive adhesive. The front waist region 30 is provided with a flexible target tape strip 56 on which the free end portions 55 of the tape fasteners 54 are releasably anchored. The target tape strip 56 is shaped in a rectangle which is relatively long in the transverse direction and made of plastic film. The target tape strip 56 is permanently attached to the outer surface of the backsheet 27.

Figure 8:
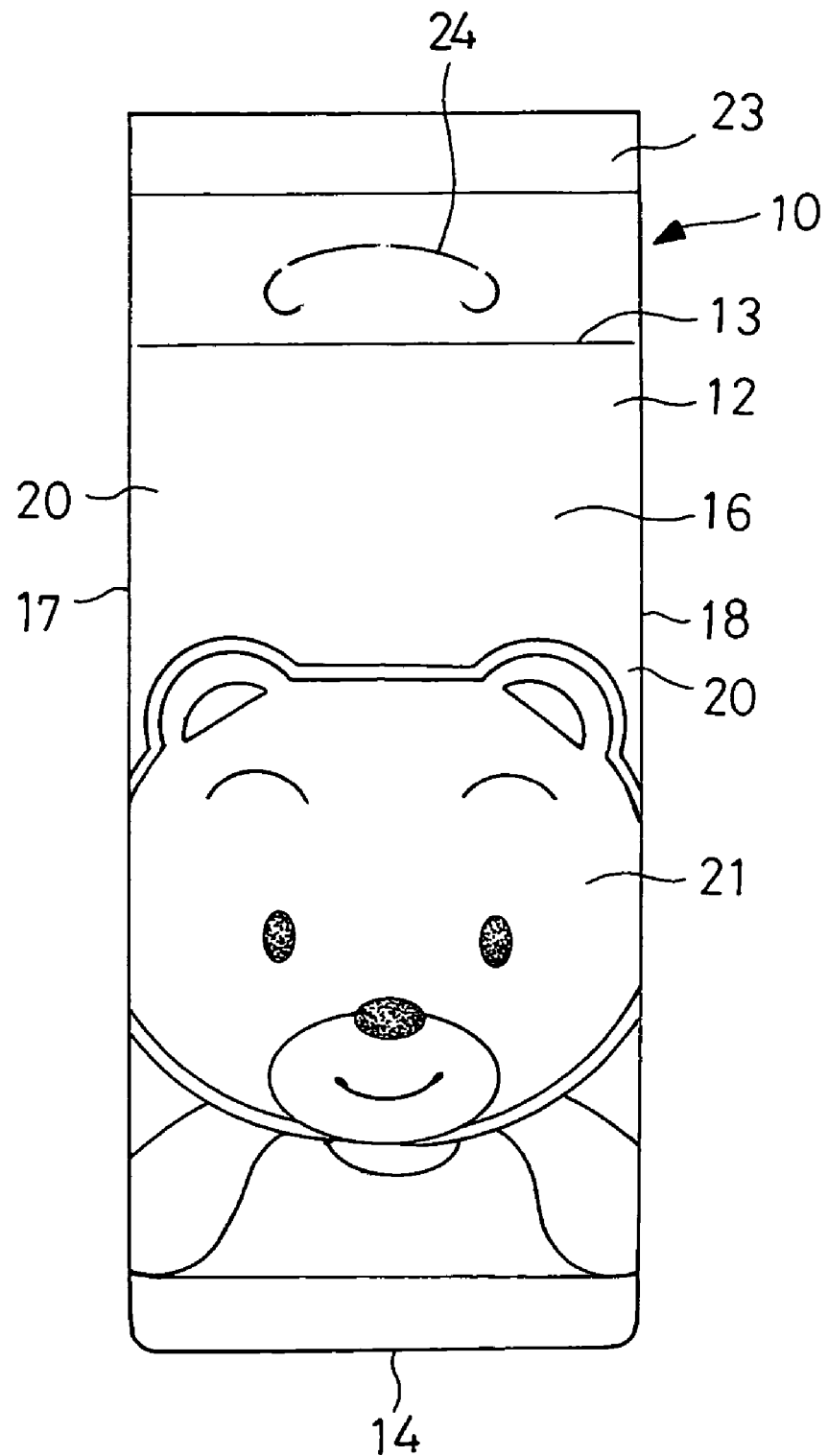
FIG. 8 is a perspective view of the package as viewed from the side of the rear wall.
Figure 9:
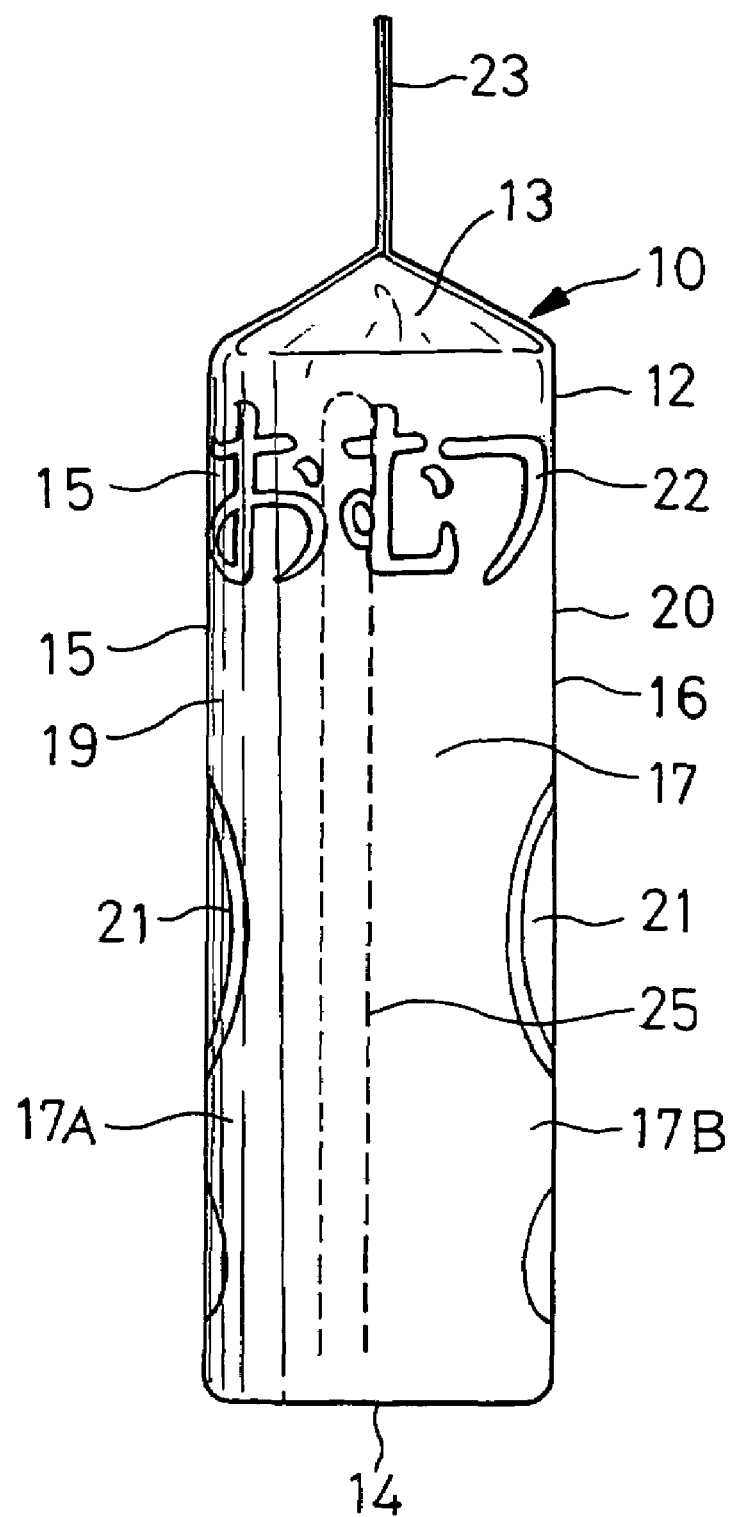
FIG. 9 is a perspective view of the package as viewed from the side of one of the side walls.
Figure 10:
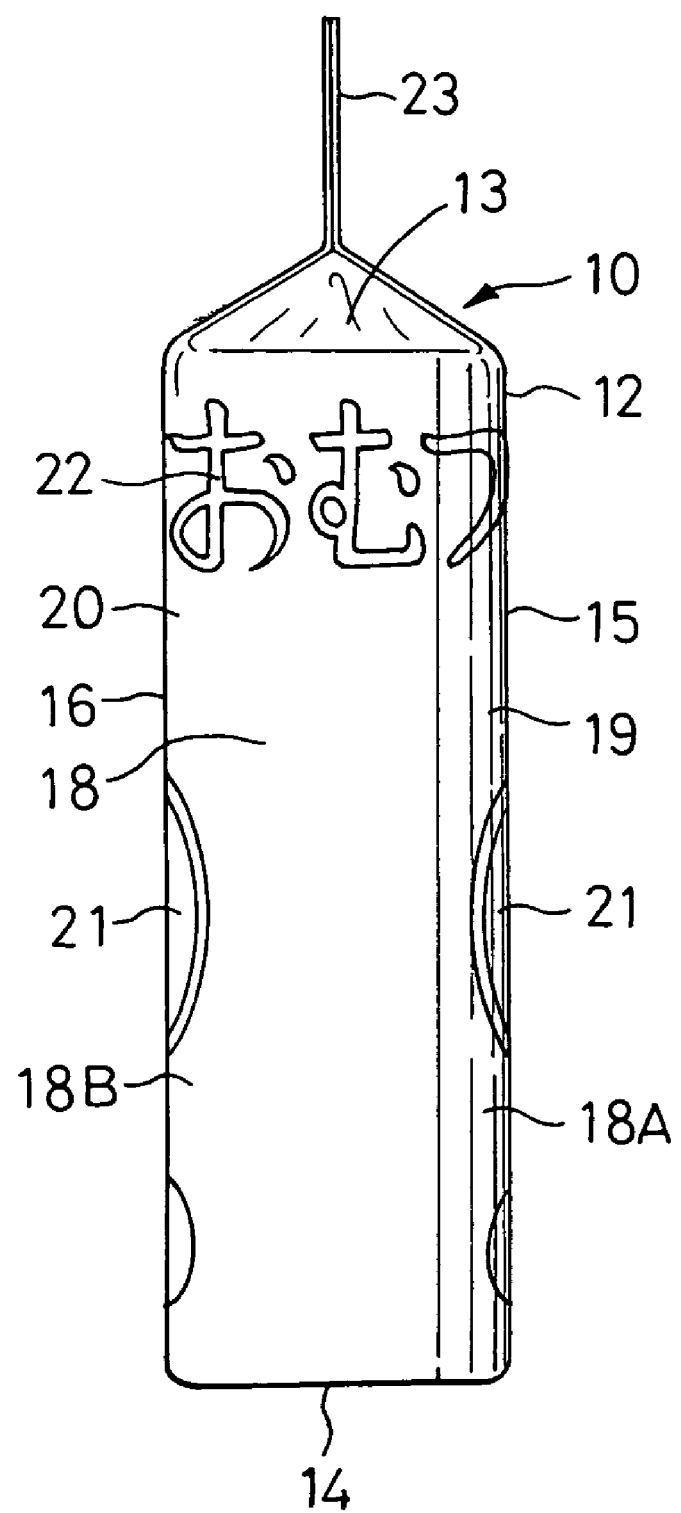
FIG. 10 also is a perspective view of the package as viewed from the side of one of the side walls.

FIG. 7 is a perspective view of the package 10 as viewed from the side of the front wall 15, FIG. 8 is a perspective view of the package 10 as viewed from the side of the rear wall 16, FIG. 9 is a perspective view of the package 10 as viewed head-on from the side of one of the side walls 17 and FIG. 10 also is a perspective view of the package 10 as viewed head-on from the side of one of the side walls 17. In this package 10, the radius of curvature at the corners 19 is longer than the radius of curvature at the corners 20, so the range in which the package 10 can be visually recognized head-on from the side of the front wall 15 is correspondingly larger than the range in which the package 10 can be visually recognized head-on from the side of the rear wall 16. In other words, the regions 17A, 18A of the side walls 17, 18 put aside toward the front wall 15 can be seen head-on from the side of the front wall 15 and therefore the outer surface of the package 10 can be visually recognized in a relatively large range as seen head-on from the side of the front wall 15. A range in which the front wall 15 can be visually recognized head-on from the side of the side wall 17, 18 is larger than a range in which the front wall 15 can be visually recognized head-on from the side of the rear wall 16. In other words, the region of the front wall 15 put aside toward the side wall 17, 18 can be visually recognized head-on from the side wall 17, 18 and the outer surface of the package 10 can be visually recognized head-on from the side of the side wall 17, 18 in a relatively large range.

In the package 10, the corners 19 at which the front wall 15 crosses the side walls 17, 18 is more noticeably rounded than the corners 20 at which the rear wall 16 crosses the side walls 17, 18, so the impression given by the package 10 as seen head-on from the side of the front wall 15 is remarkably different from the impression given by the package 10 as seen head-on from the side of the rear wall 16. Compared to the package shaped in rectangular hexahedron, the improved shape of the package 10 according to the invention can attract the attention of the consumer and leave the consumer with vivid impression. This package 10 not only improves its advertising function and quality displaying function but also functions to display the article manufacturer. In this way, there is no anxiety that the manufacturer of the article might be confused with the any other manufacturers.

When the front wall 15 of the package 10 is seen head-on, the entire image 21 of bear's head can be seen as will be apparent from FIG. 7. When the rear wall 16 of the package 10 is seen head-on, transversely opposite lateral portions of the image 21 of bear's head get chipped at the corners 20 and the image 21 can not be fully seen as will be apparent from FIG. 8. When the side wall 17, 18 of the package 10 is seen head-on, the letters 22 meaning "diaper" can be fully seen. The outer surface of the package 10 can be visually recognized in a relatively large range as seen head-on from the front wall 15 or from the side wall 17, 18 so that even if the display elements 21, 22 are printed continuously on the front wall 15 and the regions 17A, 18A of the side walls 17, 18 put aside toward the front wall 15 or continuously on the side walls 17, 18 and the region 15A of the front wall 15 put aside toward the side walls 17, 18, it is not apprehended that these display elements 21, 22 might get chipped at the corners 19 when the package 10 is seen head-on from the side of the front wall 15 or the side walls 17, 18. Thus it is possible to print the display elements 21, 22 each larger than each of the front wall 15 and the side walls 17, 18 on these walls 15, 17, 18 without getting chipped at the corners 19.

Within the package 10, the waist-surrounding front and rear end portions 33, 34 of the diapers 11 forming the first through fourth rows 40A, 40B, 40C, 40D aligned one with another between the side walls 17, 18 face the front wall 15. Therefore there is no anxiety that the front and rear end portions 33, 34 might be irregularly bent and these front and rear portions 33, 34 might be formed with a plurality of irregular gathers as the diaper package in which the front and rear end portions 33, 34 arranged in each pair of the adjacent rows of these rows 40A, 40B, 40C, 40D bear against one another in the vertical direction is the case. In each pair of the adjacent rows, the lateral portions 35 bear against one another in the vertical direction but major part of these lateral portions 35 are folded inward as viewed in the transverse direction of the diapers 11. Consequently, it is unlikely that the lateral portions 35 might be irregularly bent and formed with a plurality of irregular gathers.

In the package 10, the corners 19 at which the front wall 15 crosses the side walls 17, 18 define a radius of curvature in a range of 25 to 500 mm and the corners 20 at which the rear wall 16 crosses the side walls 17, 18 define a radius of curvature in a range of 5 to 50 mm. Preferably, the corners 19 define a radius of curvature in a range of 50 to 500 mm and a difference between the radii of curvature defined by the corners 19 and the corners 20 (i.e., radius of curvature for the corners 19 minus radius of curvature for the corners 20) is 20 mm or more. If the radius of curvature defined by the corners 19 is less than 25 mm, the range in which the package 10 can be visually recognized head-on from the side of the front wall 15 will be unacceptably limited and it will be impossible for the consumer to see the outer surface of the package 10 in a wide range head-on from the side of the front wall 15 as well as head-on from the side of the side wall 17, 18. In addition, if the radius of curvature defined by the corners 19 is less than 25 mm, the display elements 21, 22 printed continuously on the front wall 15 and the side walls 17, 18 will get chipped at the corners 19 and can not be fully recognized.

The diapers 11 may be packed within the packing bag 12 to form less or more than four rows. While FIG. 6 illustrates the embodiment in which each of the rows 40A, 40B, 40C, 40D contains fourteen diapers 11, the number of the diapers 11 in each of the rows is not limited to fourteen but may be either less than fourteen or more than fourteen. However, each of these rows 40A, 40B, 40C, 40D preferably contains eight or more diapers 11.

While the diaper package 10 has been described to pack therein the open-type diapers 11, it is possible for the package to pack therein the pants-type diapers having the front and rear waist regions previously connected to form a waist-hole and a pair of leg-holes. In the case of the pants-type diapers, the transversely opposite lateral portions of the front and rear waist regions are folded back onto the outer surface of the front or rear waist region and packed in this state in the space surrounded by the walls 13, 14, 15, 16, 17.

The display elements are not limited to the images 21 of bear's head or the letters 22 meaning "diaper" but the other images, letters, symbols, patterns, colors or a combination thereof may be used. The images, letters, symbols or patterns may be colored or achromatic. The images are not limited to particular shapes and include not only pure art settled on the subject matter of personality, landscape or animal but also applied art. The letters include all letterings such as hieroglyph, ornamental letters and fancy letters.

The packing bag 12 is an oriented plastic film of thermoplastic synthetic resin. The synthetic resin may be selected from the group consisting of polyester-based synthetic resin, polyacrylonitril-based synthetic resin, polyvinyl chloride-based synthetic resin, polyethylene-based synthetic resin, polypropylene-based synthetic resin and polystyrene-based synthetic resin. For permanently bonding the film 12 to itself, suitable welding technique such as heat-sealing or sonic sealing.

Stock materials for the topsheet 26 is not limited to hydrophobic fibrous nonwoven fabrics but may be selected also from the group consisting of a perforated hydrophobic fibrous nonwoven fabric and a finely perforated plastic film. Stock materials for the backsheet 27 may be selected from the group consisting of a hydrophobic fibrous nonwoven fabric, a breathable liquid-impervious plastic film and a composite nonwoven fabric(s) comprising two or more hydrophobic fibrous nonwoven fabric laminated one with another. It is also possible to form the backsheet and the leak-barrier sheets 28 using a composite nonwoven fabric comprising a melt blown nonwoven fabric having a high water-resistance and a spun bond nonwoven fabric laminated on both surfaces or one surface of the melt blown nonwoven fabric (SM nonwoven fabric, SMS nonwoven fabric, SMMS nonwoven fabric).

The fibrous nonwoven fabric may be selected from those obtained by spun lace-, needle punch-, melt blown-, thermal bond-, spun bond- and chemical bond-processes. Component fibers of these nonwoven fabric may be selected from a group consisting of polyester-, polyacrylonitril-, polyvinyl chloride-, polyethylene-, polypropylene- and polystyrene-based fibers. It is also possible to use, as the component fiber, core-sheath conjugate fiber, side-by-side conjugate fiber, modified macaroni fiber, microporous fiber and fused type conjugate fiber.

Permanently bonding the top- and backsheets 26, 27 to each other, permanently bonding the leak-barrier sheets 28 to the sheets 26, 27, permanently bonding the core 29 to the sheets 26, 27 and permanently bonding the elastic members 46, 53 to the sheets 26, 27, 28 may be achieved using adhesive or welding technique such as heat-sealing or sonic sealing. The adhesive may be selected from a group consisting of hot melt adhesive, polyacrylic adhesive and rubber-based adhesive.

What is claimed is:

1. A diaper package composed of a plurality of disposable diapers each comprising a liquid-pervious topsheet, a liquid-impervious backsheet and a liquid-absorbent core having stiffness higher than these sheets and interposed between these two top- and backsheets, and a flexible packing bag adapted to pack said plurality of diapers wherein each of said diapers has first and second waist regions and a crotch region along which said first and second waist regions are contiguous to each other and a waist-surrounding end portion lying opposed to said crotch region so as to define upper end portions of said first and second waist regions, respectively and wherein said packing bag defines top and bottom walls spaced from each other in a vertical direction, first and second walls opposed to each other and extending between said top and bottom walls and a pair of side walls extending between said top and bottom walls so that a plurality of said diapers each folded back along said crotch region are compactly packed within a space surrounded by these walls, said diaper package further comprising:

a plurality of said diapers being arranged with the waist regions thereof placed against one another to be arranged between said side walls to form a row extending between said side walls so that the respective crotch regions' bottoms aligned one with another between the side walls face said second wall and the waist-surrounding end portions of the respective diapers aligned one with another between said side walls face said first wall;

a radius of curvature of a corner at which said first wall and said side walls cross each other is longer than a radius of curvature of a corner at which said second wall and said side walls cross each other so that a range in which said package can be visually recognized head-on from the side of said first wall is larger than a range in which said package can be visually recognized head-on from the side of said second wall.

2. The diaper package as set forth in claim 1, wherein desired display elements are printed on outer surfaces at least said first wall and said side walls.

3. The diaper package as set forth in claim 1, wherein at least two rows of said diapers are stacked on each other in the vertical direction and, in each of these rows stacked on each other, said crotch regions of the respective diapers are aligned between said side walls and face said second wall and said waist-surrounding end portions of the respective diapers are aligned between said side walls and face said first wall.

4. The diaper package as set forth in claim 1, wherein the radius of curvature of the corner at which said first wall crosses said side walls is in a range of 25 to 500 mm and the radius of curvature of the corner at which said second wall crosses said side walls is in a range of 5 to 50 mm.

5. The diaper package as set forth in claim 1, wherein a total thickness dimension of said first waist region, second waist region and crotch region is larger than a thickness dimension of said waist-surrounding end portion in each of said diapers and stiffness of said first waist region, second waist region and crotch region is higher than stiffness of said waist-surrounding end portion in each of said diapers.

6. The diaper package as set forth in claim 1, wherein said packing bag has a cylindrical shape prior to packing said diapers therein and this cylindrical packing bag is deformed so as to form said first and second walls and said side walls as said diapers are packed within the space surrounded by a cylindrical wall of said packing bag.

* * * * *